(12) United States Patent
Takahashi et al.

(10) Patent No.: US 7,956,324 B2
(45) Date of Patent: Jun. 7, 2011

(54) CHARGED PARTICLE BEAM APPARATUS FOR FORMING A SPECIMEN IMAGE

(75) Inventors: Noritsugu Takahashi, Kokubunji (JP); Muneyuki Fukuda, Kokubunji (JP); Hideo Todokoro, Hinode (JP); Mitsugu Sato, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 339 days.

(21) Appl. No.: 12/155,038

(22) Filed: May 29, 2008

(65) Prior Publication Data
US 2008/0302962 A1    Dec. 11, 2008

(30) Foreign Application Priority Data

Jun. 7, 2007   (JP) ................................ 2007-151752

(51) Int. Cl.
*H01J 37/26*  (2006.01)

(52) U.S. Cl. .................... 250/306; 250/307; 250/492.3

(58) Field of Classification Search .................. 250/306, 250/307, 309, 310, 311, 492.1, 492.2, 492.21, 250/492.22, 492.3; 430/296, 297, 298; 382/141, 382/144, 145, 147, 148, 149, 173, 181
See application file for complete search history.

(56) References Cited

U.S. PATENT DOCUMENTS

| 6,852,973 B2 | 2/2005 | Suzuki et al. |
| 7,075,077 B2 | 7/2006 | Okuda et al. |
| 2005/0146714 A1 | 7/2005 | Kitamura et al. |
| 2005/0230618 A1* | 10/2005 | Onishi et al. ................. 250/310 |
| 2005/0285034 A1* | 12/2005 | Tanaka et al. ................ 250/310 |
| 2006/0243905 A1* | 11/2006 | Yamaguchi et al. .......... 250/307 |

FOREIGN PATENT DOCUMENTS

| JP | 11-120951 | 4/1999 |
| JP | 11-243122 | 9/1999 |
| JP | 2003-303564 | 10/2003 |
| JP | 2004-227886 | 8/2004 |
| JP | 2005-277395 | 10/2005 |
| JP | 2005-285746 | 10/2005 |

* cited by examiner

*Primary Examiner* — David A Vanore
*Assistant Examiner* — Nicole Ippolito Rausch
(74) *Attorney, Agent, or Firm* — Antonelli, Terry, Stout & Kraus, LLP.

(57) ABSTRACT

The invention provides a charged particle beam apparatus capable of preventing image errors in a display image and capturing a clear display image. A display image displayed on a display unit has a rectangular shape having sides that are substantially parallel to coordinate axes of a rectangular coordinate system determined by wafer alignment. A charged particle beam is radiated onto an area including a display image in a direction that is not parallel to the coordinate axes of the reference rectangular coordinate system to scan the area. Then, among image information obtained by scanning, only information of a position within the display image is displayed on the image display unit. In this way, a clear display image without brightness variation is obtained.

11 Claims, 11 Drawing Sheets

CHARGED PARTICLE BEAM APPARATUS FOR FORMING A SPECIMEN IMAGE

CLAIM OF PRIORITY

The present application claims priority from Japanese patent application JP 2007-151752 filed on Jun. 7, 2007, the content of which is hereby incorporated by reference into this application.

BACKGROUND OF THE INVENTION

1. Field of the Invention

The present invention relates to a charged particle beam apparatus, and more particularly, to a technique for measuring the shape and dimensions of a circuit pattern formed on a specimen or inspecting the circuit pattern.

2. Description of the Related Art

A technique for inspecting or reviewing the state of a circuit pattern formed on a semiconductor wafer is important to improve the yield and reliability of the products. The inspection or review is performed by an apparatus using light or an apparatus using charged particle beams, such as electron beams. In particular, in recent years, with the size reduction of semiconductor devices, the inspection and review processes using charged particle beams have become important. However, the surface of the semiconductor wafer during a manufacturing process is formed of an insulating film, such as a silicon oxide, a silicon nitride, an organic material, or a high-k material. Therefore, when a charged particle beam is radiated onto the surface of the wafer, the surface of the wafer is electrified, which changes the trajectory of signal particles generated from the surface. Particularly, the change in the trajectory of the signal particles is noticeable at the boundary between an area in which the charged particle beam is radiated and an area in which no charged particle beam is radiated, that is, at the boundary between a charged-up area and a neutron area. As a result, an image error, such as brightness variation, occurs in an acquired image formed by the signal particles. In addition, the image error, such as the brightness variation, may occur at the center of the acquired image due to the relationship between the structure or arrangement of a pattern and the scan direction of the charged particle beam. Since this image error deteriorates inspection accuracy, it is important to reduce the image error.

As an example of the technique for reducing the image error, Japanese Unexamined Patent Application Publication (JP-A) Nos. 2004-227886 and 11-120951 disclose a technique that scans an area larger than a display area of an acquired image with an electron beam to acquire an image and trims out a necessary area from the acquired image. In addition, as a technique for avoiding the influence of a contrast variation caused by the arrangement of a pattern, JP-A No. 2003-303564 and JP-A No. 2005-285746 disclose a technique that radiates an electron beam in a direction that is inclined at a predetermined angle in the plane with respect to the scan direction of the electron beam when an image is captured, thereby performing auto-focus.

BRIEF SUMMARY OF THE INVENTION

In the technique disclosed in JP-A No. 2004-227886, a defect position is searched from an acquired defect image for search such that the scan area of an electron beam is matched with the display area of the acquired image, and then the acquired image is trimmed such that the scan area of the electron beam corresponds with the scan area when the defect image for search is captured, thereby acquiring the defect image for observation. FIG. 2 is a diagram illustrating the relationship between the display image and the acquired image when the defect image for observation is acquired. Scanning 104 with an electron beam is performed on a pattern 101 formed on a specimen in the direction of an arrow, thereby acquiring an acquired image 103, and a necessary area is trimmed out from the acquired image to obtain a display image 102. In this technique, the capture magnification of the acquired image 103 is the same as that of the defect image for search. In this technique, since the edge of the defect image for observation does not correspond to the boundary between the area in which the electron beam is radiated and the area in which no electron beam is radiated, it is possible to prevent image errors in the edge of the image, but it is difficult to prevent image errors at the edge of the defect image for search. In the technique disclosed in JP-A No. 11-120951, since the technique shown in FIG. 2 can be applied to all the display images, it is possible to prevent image errors at the edge of the display image of the defect image for search. However, these techniques cannot reduce image errors, such as brightness variation, caused from the relationship between the structure or the arrangement of a pattern and the scan direction of the charged particle beam.

JP-A No. 2003-303564 and JP-A No. 2005-285746 disclose a technique that controls the scan direction of an electron beam while auto-focusing such that horizontal and vertical components of the electron beam are inclined with respect to the direction in which chips are arranged on a wafer. However, in the technique, since the electron beam radiated by the above-mentioned method is not used as a display image, it is difficult to improve the contrast of the display image.

When an image is captured in the scan direction as in the above-mentioned technique, the display direction of the image varies in correspondence with the scan direction. When the display direction varies, erroneous recognition of display information is likely to occur in an image having directivity such as bump/bent information.

An object of the invention is to provide a charged particle beam apparatus capable of preventing an image error in a display image, capturing a clear image without brightness variation, improving a defect recognition rate during auto review, and preventing erroneous recognition of display information.

In a defect inspection and review system that scans a specimen with a charged particle beam to capture a charged particle beam image, generally, horizontal and vertical directions of a display image are aligned with the rectangular coordinate axes that are determined by wafer alignment. In this case, the vertical and horizontal directions of an acquired image are aligned with the scan direction of the charged particle beam. In many cases, in the display of a regular pattern, such as a straight pattern on a display image, the longitudinal direction of the straight pattern is aligned with one of the coordinate axes orthogonal to each other. The inventors found that a clear display image was acquired by scanning a region including a display area with a charged particle beam in a direction that is inclined with respect to the rectangular coordinate axes determined by wafer alignment, thereby acquiring a charged particle beam image, and extracting from, the charged particle beam image, an image obtained by radiating the charged particle beam in the direction of the rectangular coordinate axes.

That is, in order to achieve the object, an aspect of the invention provides a charged particle beam apparatus that scans a specimen with a charged particle beam in a direction that is different from the coordinate axes of a rectangular coordinate system (a reference rectangular coordinate system of the charged particle beam apparatus), which is a standard for wafer alignment (for controlling the position of a specimen to be measured in the plane) or for controlling the direction in which the charged particle beam is radiated, detects secondary signals generated from the specimen by scanning, stores image information obtained from the detected secondary signals in an image formation storage unit, selectively reads, from the image formation storage unit, image information of an image display area having sides that are aligned with the axes of the reference rectangular coordinate system, and displays the read image information on an image display unit.

According to the above-mentioned aspect of the invention, it is possible to provide a charged particle beam apparatus capable of preventing image errors occurring at, for example, the boundary between a charged-up area and a neutron area in a display image, and acquiring a clear image without brightness variation.

DETAILED DESCRIPTION OF THE INVENTION

Hereinafter, exemplary embodiments of the invention will be described with reference to the accompanying drawings.

Figure 1:
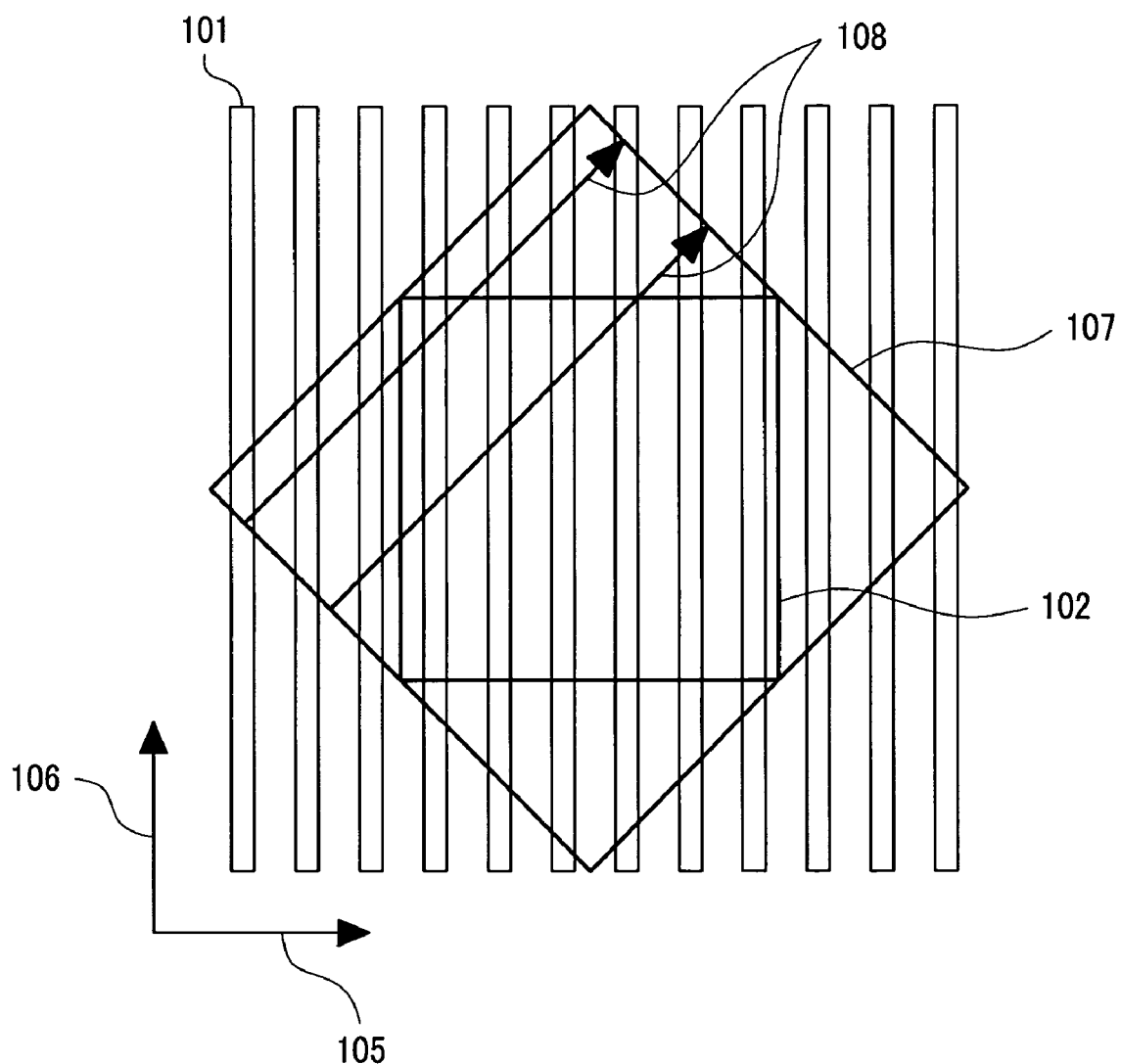
FIG. 1 is a diagram schematically illustrating the relationship between the scan area of a charged particle beam and a display image according to an embodiment of the invention.
Figure 2:
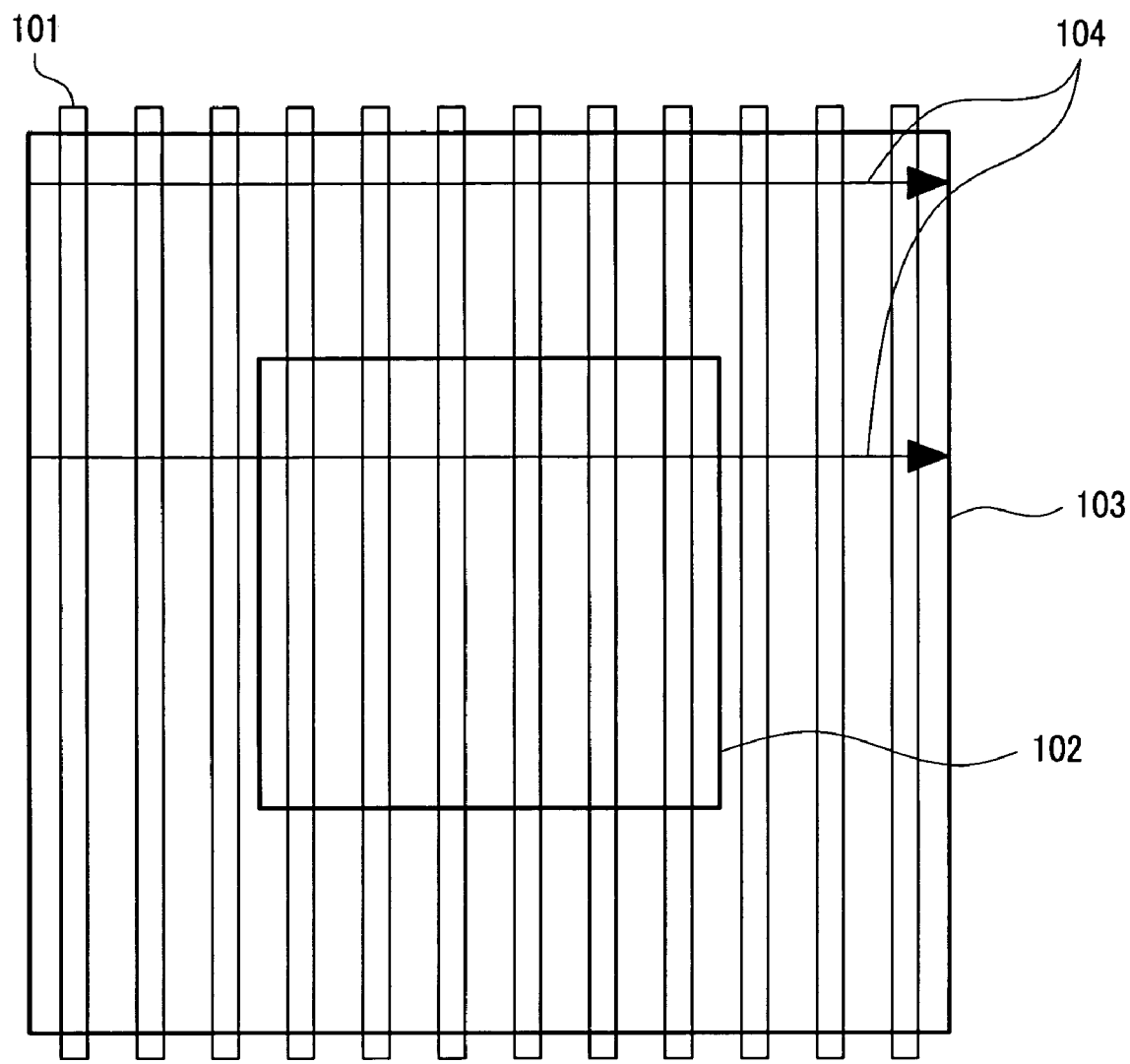
FIG. 2 is a diagram schematically illustrating the relationship between the scan area of a charged particle beam and a display image according to related art.

First, the basic concept of the invention will be described with reference to FIG. 1. In FIG. 1, for example, in a reference rectangular coordinate system including a first coordinate axis 105 and a second coordinate axis 106 determined by wafer alignment, a display image 102 is formed to correspond to a rectangular shape having sides that are substantially in parallel to the first coordinate axis 105 and the second coordinate axis 106. Scanning 108 with a charged particle beam is performed in a direction (oblique direction) that is different from the first coordinate axis 105 and the second coordinate axis 106. Among image information obtained by irradiating an area 107 with charged particle beams by the scanning 108, only information included in a display image area of the display image 102 is displayed on an image display unit of a charged particle beam apparatus.

First Embodiment

As a first embodiment, a defect review system in which the inclination angle of the scan direction of charged particle beams is fixed will be described. The defect review system means a charged particle beam apparatus that acquires (reviews) high-resolution image information of defects of interest on a specimen to be reviewed. In many cases, an inspection apparatus other than an appearance inspection apparatus is generally used to detect positional information of an important position to be inspected, and a review operation is performed on the basis of the positional information. As the specimen to be reviewed, semiconductor wafers having a circuit pattern formed thereon are generally used, but bare wafers without patterns, chips or pieces divided from wafers, or liquid crystal panels or magnetic disk media may be used as the specimen. Examples of the important position to be reviewed include positions where electric defects, such as the breaking of lines or defects in contact holes, occur and positions where shape defects, such as the adhesion of foreign materials on the surface of a specimen or the distortion of patterns, occur.

A scanning electron microscope is mainly used as the charged particle beam apparatus, serving as an image capturing apparatus. The term 'inclination angle' means an angle that is defined by a reference rectangular coordinate system of the charged particle beam apparatus in order to control the in-plane position of a wafer, which is a specimen to be inspected, or the scan direction of charged particle beams. The inclination angle may be stored in a control system of the apparatus beforehand, or it may be input through an input unit by an apparatus operator.

In the defect review system according to the first embodiment, a primary electron beam is radiated onto a specimen to scan the specimen, and signal electrons emitted from the specimen are divided according to the angular direction. Then, independent signal detectors detect the divided signal electrons, and assign the brightness of pixels corresponding to the emission positions according to the number of electrons detected, thereby forming an image. The images include an image having a large number of information signals emitted in the normal direction of the specimen (hereinafter, referred to as a surface information image) and an image having a large number of information signals emitted at a large angle with respect to the normal direction of the specimen (hereinafter, referred to as a bump/dent information image). The view directions of the two kinds of acquired images are both aligned with the normal direction of the specimen. However, the surface information image is displayed such that it has a light source in the same direction as the view direction, and the bump/dent information image is displayed so as to have a light source in direction that is inclined with respect to the view direction, so that bumps/dents on the surface of the specimen are enhanced. The contrast direction of the dump/dent information image depends on the arrangement of a detector for detecting the image. Therefore, when the display direction of the image is changed, the positional relationship of the contrast on a display screen is changed with the variation in the display direction. That is, for example, when the display direction is rotated 180 degrees, the positional relationships of the contrast before and after the rotation are reversed. This causes the recognition errors of bumps/dents when visually determining bumps/dents in the contrast direction displayed on the image. In addition, when the display image is rotated by an angle other than 180 degrees, the positional relationship of the contrast is also changed, which makes it difficult to determine bumps/dents. Therefore, it is necessary to maintain the display image in a fixed display direction.

Figure 3:
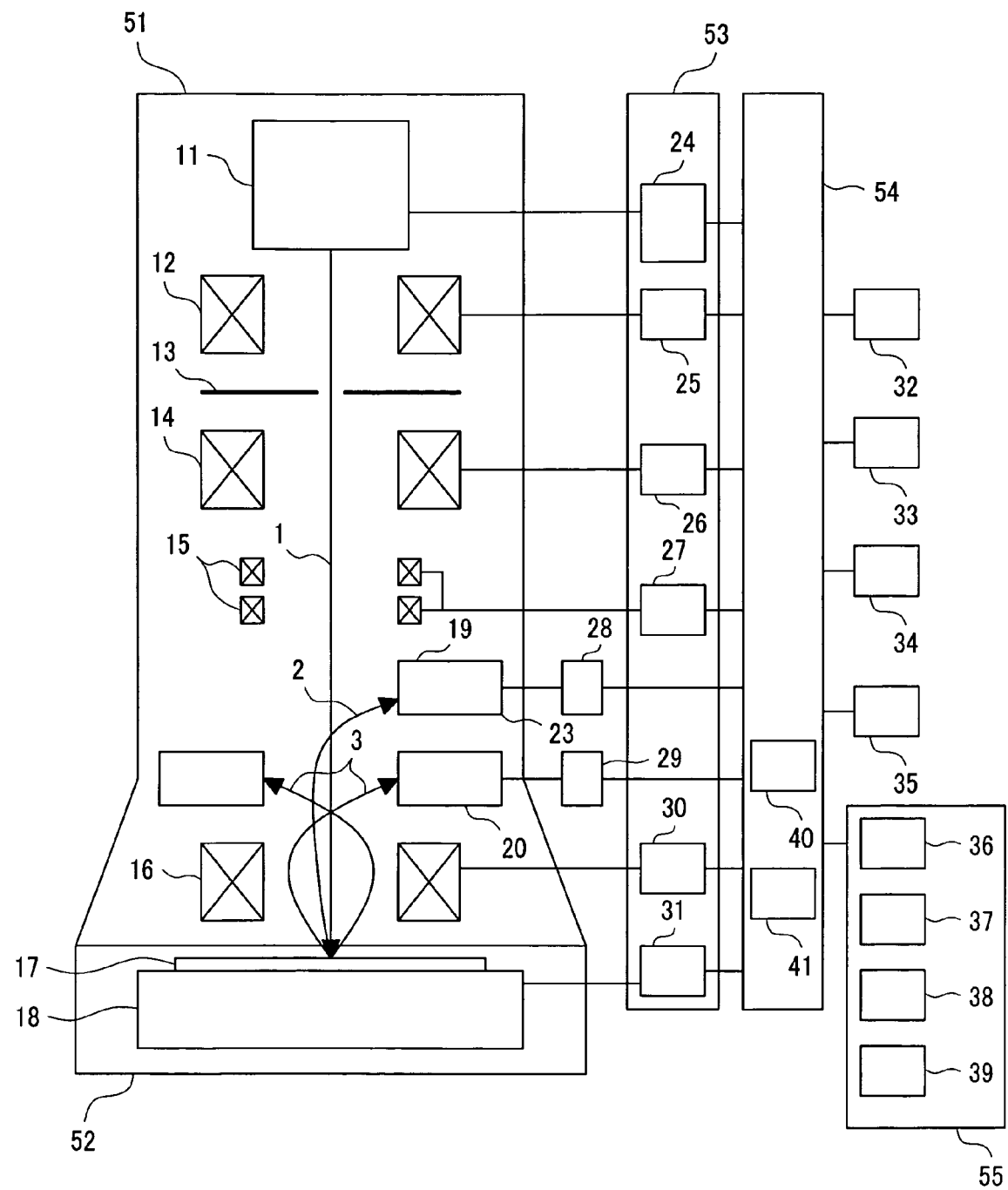
FIG. 3 is a diagram illustrating the overall structure of a defect review system according to a first embodiment of the invention.

FIG. 3 is a diagram schematically illustrating the configuration of the defect review system according to this embodiment. The defect review system shown in FIG. 3 includes: a scanning electron microscope having an electronic optical system column 51 and a specimen chamber 52; a power supply unit 53 that supplies various driving voltage and currents to the electronic optical system column 51; an arithmetic unit 54 that controls the overall operation of the system; an image display unit 32 that is attached to the arithmetic unit 54; an image storage unit 33 that temporarily stores information of an image displayed on the image display unit 32; a review information storage unit 34 that stores various information required for a review process, such as an inclination angle, display magnification, and positional information of defects on a wafer; an input unit 35 that allows a user to input various parameters required to operate the apparatus; and an image forming unit 55 that has various image processing functions, such as a function of generating a scan waveform for scanning in the oblique direction (a driving signal for a scan deflector) and a function of forming a desired image on the basis of output signals from a secondary electron detector. The arithmetic unit 54 includes an angle converting unit 40 and an image address generating unit 41. The image forming unit 55 includes an image formation memory 36, which is an image formation storage unit, a scan waveform forming unit 37, an image processing unit 38, and a signal path switching unit 39. In this embodiment, the angle converting unit 40 and the image address generating unit 41 are components of the arithmetic unit 54, but they may be provided as components of the image forming unit 55. The arithmetic unit 54 and the image forming unit 55 may be integrally formed, and the arithmetic unit 54 and the image forming unit 55 may be generically called a processing unit.

The power supply unit 53 is a set of control power sources for components of the electronic optical column 51 and a specimen stage 18, and includes a high-voltage control power source 24, lens control power sources 25 and 26, a deflection lens control power source 27, an objective lens control power source 30, and a specimen voltage control power source 31 that applies a voltage to the specimen stage 18.

A primary electron beam 1 emitted from an electronic source 11 that is controlled by the high-voltage control power source 24 is focused by a first focusing lens 12 controlled by the lens control power source 25, and unnecessary ranges of the primary electron beam are removed by a throttle plate 13. Then, the primary electron beam is focused to a very small spot on a specimen 17 by a second focusing lens 14 controlled by the lens control power source 26 and an objective lens 16 controlled by the objective lens control power source 30. The primary electron beam 1 is radiated onto the specimen to two-dimensionally scan the specimen according to the dimensions of a scan area or a scan speed by a deflector coil 15, serving as a scan deflector controlled by the deflection lens control power source 27, which is a deflection control unit. That is, when a negative voltage controlled by the specimen voltage control power source 30 is applied to the specimen 17, the primary electron beam 1 radiated to the specimen 17 is decelerated. The power supply unit 53 including all of the above-mentioned power sources can be controlled in response to instructions from the arithmetic unit 54.

A secondary signal 2, such as a secondary electron generated from the specimen 17 by the radiation of the primary electron beam 1, is detected by a secondary signal detector 19, and then amplified by a signal amplifier 28. Then, the amplified secondary signal is transmitted as pixel information to the image forming unit 55. When the primary electron beam 1 is radiated, electrons are reflected from the specimen 17 in a direction that is inclined at a predetermined angle with respect to the incident direction of the primary electron beam, and a secondary signal 3 of a secondary electron is generated from the specimen 17. Then, the reflected electrons and the secondary signal 3 are detected by a bump/dent information image detector 20 and then amplified by a signal amplifier 29. Then, the amplified electrons and secondary signal are transmitted as pixel information to the image forming unit 55. The detectors 19 and 20 may be generically called a secondary signal detector.

The specimen stage 18 can independently move the specimen 17 in at least two directions of axes of the rectangular coordinate system in the plane orthogonal to the incident direction of the primary electron beam. The specimen stage 18 can read the coordinates of a review position stored in the review information storage unit 34, or the coordinates input to the input unit 35, and move the specimen 17 to the coordinates in response to instructions from the arithmetic unit 31.

Figure 4:
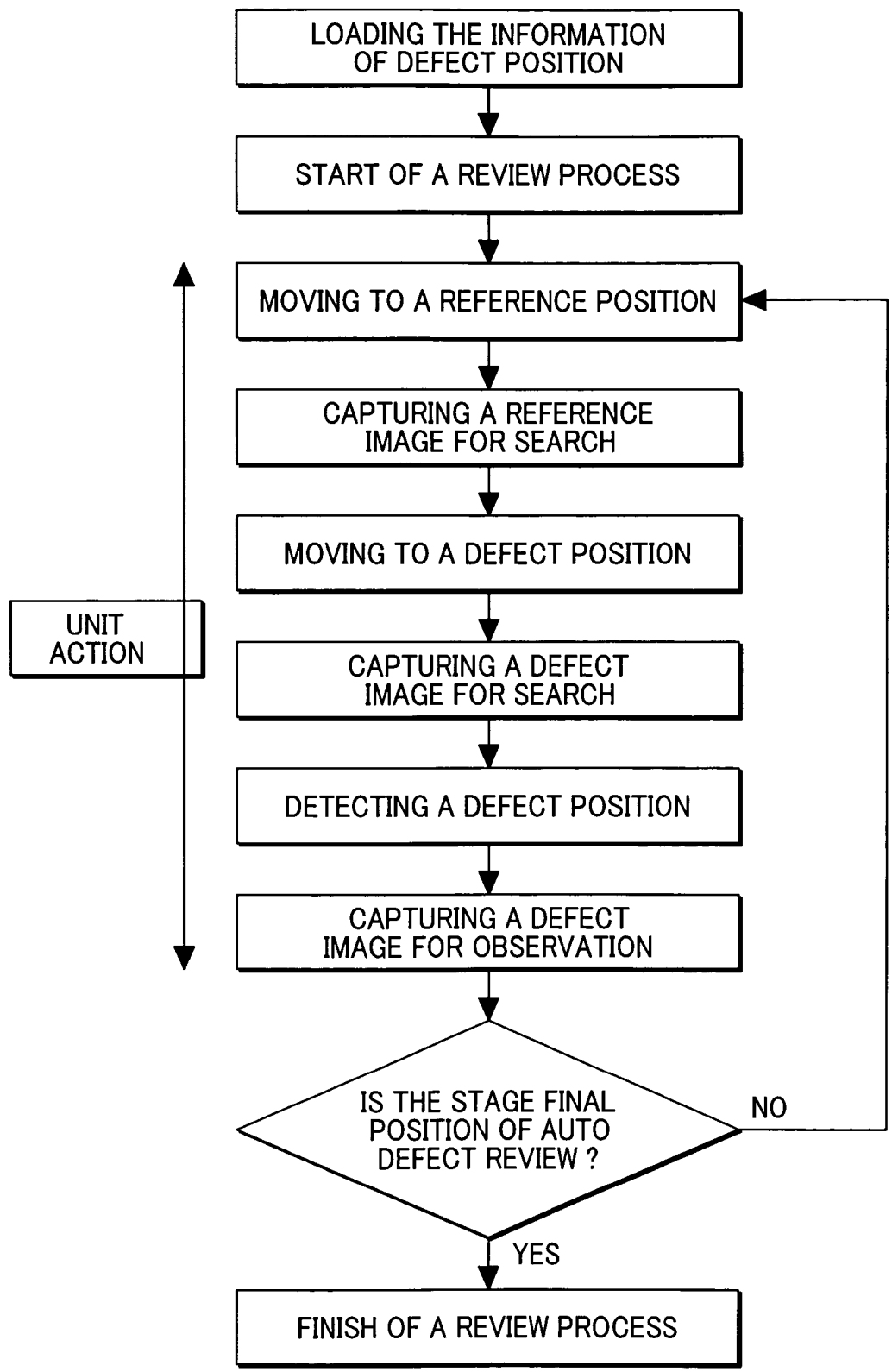
FIG. 4 is a flowchart illustrating the operation of the defect review system according to the first embodiment of the invention.

FIG. 4 is a flowchart illustrating the overall operation of the defect review system according to this embodiment. The defect review system according to this embodiment captures an image (hereinafter, referred to as a defect image for search) for searching a defect position on the basis of the acquired defect positional information and an image (hereinafter, referred to as a defect image for observation) for enlarging defects. After a review process starts, a sequence of processes of moving to a reference position for comparison with a defect position, capturing a reference image for search, moving to a defect position, capturing a defect image for search, detecting a defect position, and capturing a defect image for observation is performed in this order whenever the image of each defect position is captured. A series of processes is repeated until an image capturing area is changed from the start position of a defect review to the end position thereof whenever image capturing for a predetermined region including a defect position is completed. In this embodiment, image capturing is applied to all of the reference image for search, the defect image for search, and the defect image for observation.

Figure 5:
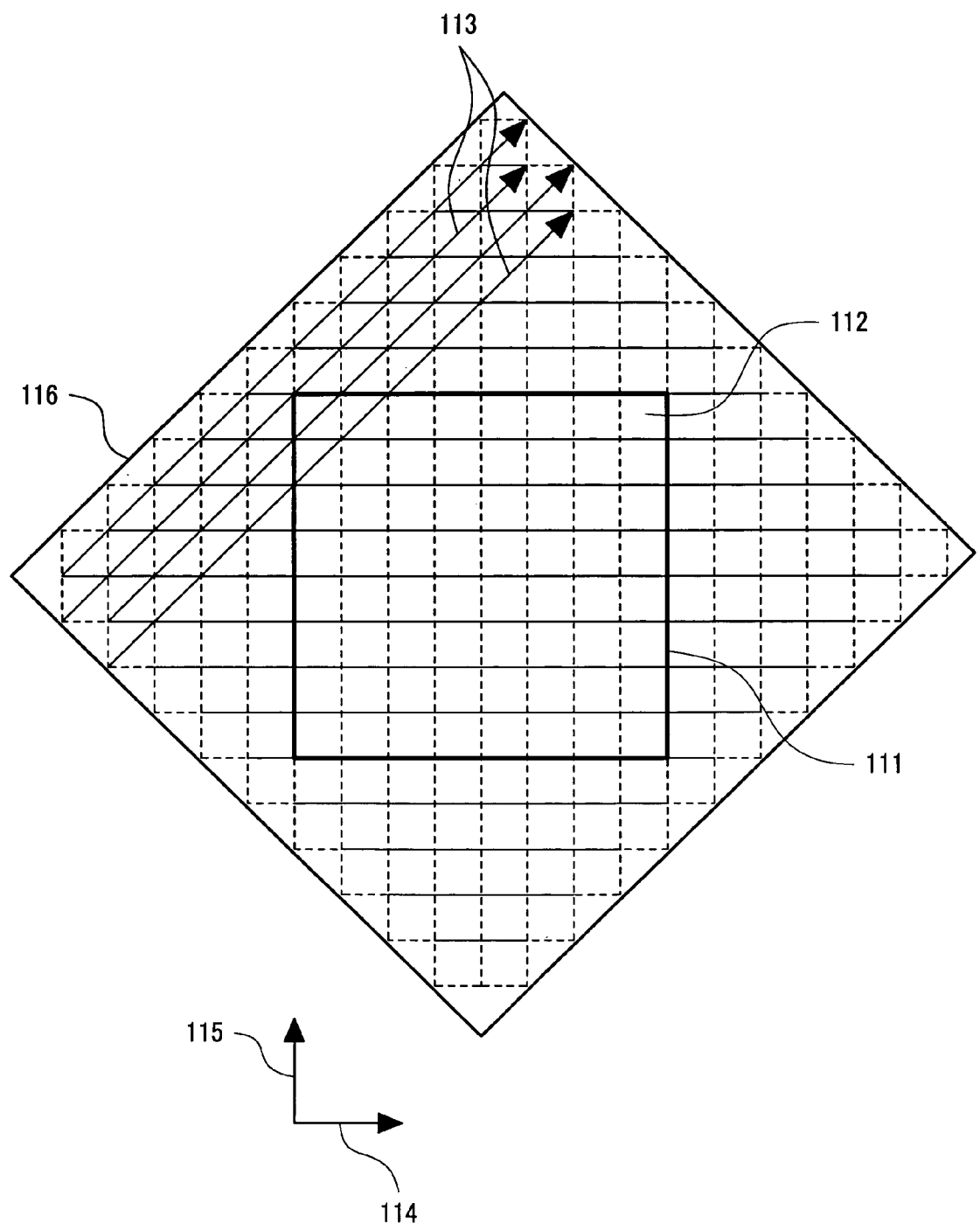
FIG. 5 is a diagram schematically illustrating an electron beam scanning method according to the first embodiment of the invention.

Next, the relationship between a display image and the scan direction of a charged particle beam in the defect review system according to this embodiment will be described with reference to FIG. 5. A scan angle θ is fixed to 45 degrees. FIG. 5 illustrates when the charged particle beams are radiated onto a portion of the specimen to be reviewed. In FIG. 5, reference numeral 116 denotes a beam scan area (which corresponds to reference numeral 107 of FIG. 1), reference numeral 113 denotes the scan trajectory of a charged particle beam, reference numeral 111 denotes a trimming area of an image displayed on the image display unit 32, reference numeral 112 denotes a pixel forming a trimming display image, and reference numerals 114 and 115 denote coordinate axes in an XY rectangular coordinate system, which is a reference coordinate system for determining an oblique scan direction (a first coordinate axis and a second coordinate axis, which correspond to reference numerals 105 and 106 of FIG. 1, respectively). Similar to FIG. 1, a certain wiring pattern is formed on the specimen to be reviewed and a longitudinal pattern is aligned with a Y-axis 115.

The trimming image 111, serving as the display image, has a substantially rectangular shape having sides that are substantially parallel to the first coordinate axis 114 and the second coordinate axis 115. The pixels 112 assigned to the scan area 116 are arranged so as to correspond to the pixels assigned to the area of the display image 111. The scanning 113 with electron beams is performed in a direction that is inclined at a predetermined angle θ with respect to the first coordinate axis 114.

In this embodiment, the scan angle θ is defined on the basis of an X-axis 114 of the reference coordinate system. The field of view of the trimming image 111 depends on the size of one pixel forming the image and the number of pixels, and the scan area 116 depends on the field of view of the trimming image 111. The size of the pixel depends on the spot diameter of a charged particle beam and the magnification of an image. Therefore, the size of the trimming image 111 and the size of the scan area 116 depend on the resolution, the review magnification, and the field of view of a review image.

Beam scanning is performed by two-dimensionally moving the radiation position of a charged particle beam in the beam scan area 116. In general, beam scanning is performed by repeating a process of sequentially moving the radiation position of the charged particle beam by a predetermined distance in a predetermined direction (for example, a first direction), in a direction (for example, a second direction) orthogonal to the predetermined direction, and in the same direction as the first direction. In the example shown in FIG. 5, the first direction is the direction of the scan trajectory 113, and the second direction is orthogonal the scan trajectory 113. The term 'scan' means the movement of the radiation position of the charged particle beam in the first direction. The term 'scan' may also mean the two-dimensional movement of the radiation position of the charged particle beam in a predetermined area. That is, the usage of the term 'scan' depends on purpose. The movement distance of the charged particle beam in the first direction may be called a 'scan width'. A coordinate system for controlling the beam radiation position of the defect review system according to this embodiment is determined by wafer alignment, and is represented by the reference coordinate systems 114 and 115.

Figure 6:
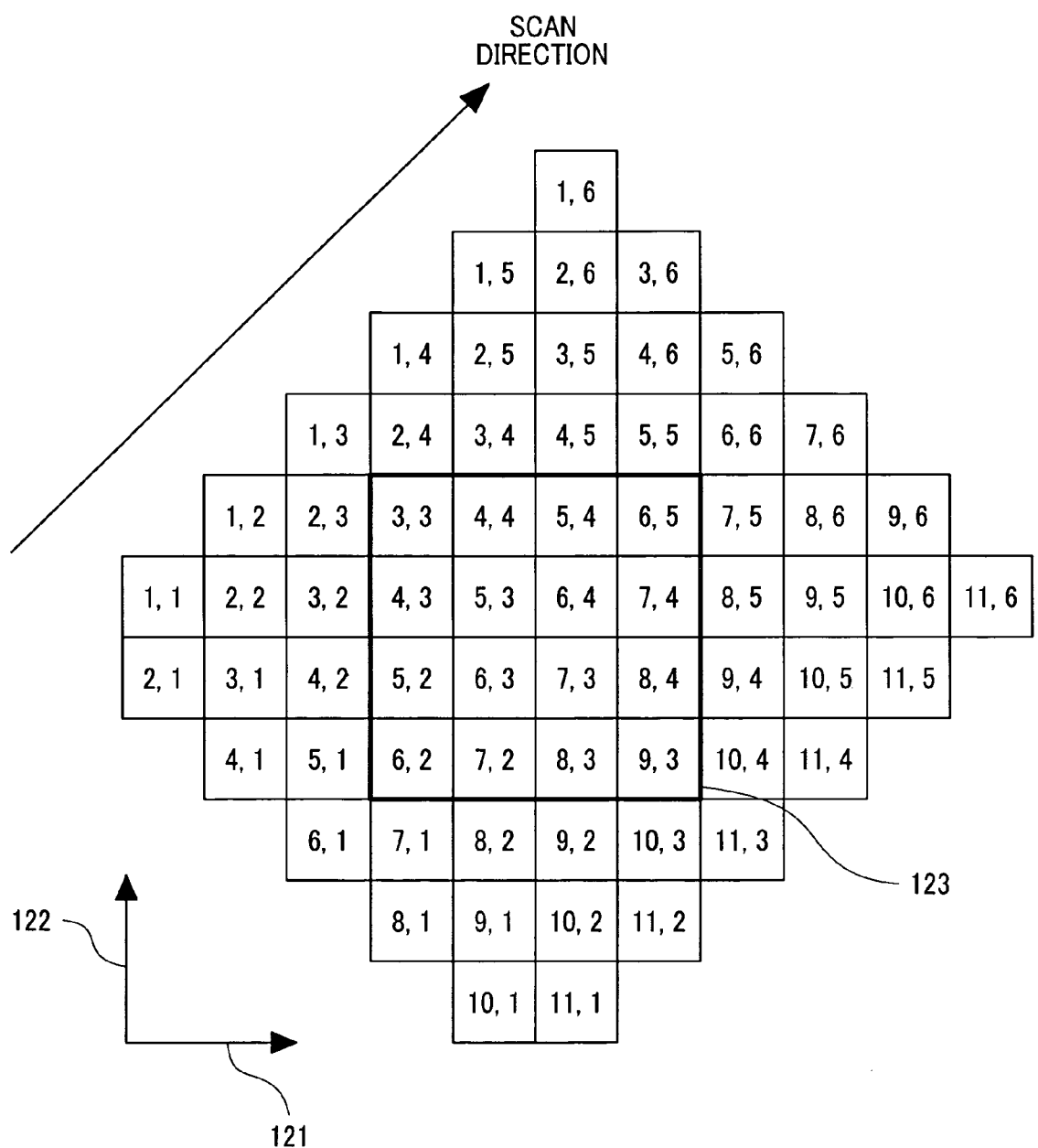
FIG. 6 is a diagram schematically illustrating a display image forming method and image signal data stored on the basis of the electron beam scanning method according to the first embodiment of the invention.

Next, a process of assigning address information to displayed pixels according to this embodiment will be described with reference to FIG. 6. For clarity of description, it is assumed that an image of 4 by 4 pixels is acquired. FIG. 6 shows addresses assigned to the scan positions when an electron beam is radiated in a direction that is inclined at an angle of 45 degrees with respect to the first coordinate axis. Each scan address is represented by two character strings. The front character string indicates the address of a scan line, and the rear character string indicates a write order address in the scan line, that is, information of a data storage order.

The scan address shown in FIG. 6 is a physical address that is virtually assigned to each pixel for easy understanding. In the actual computing process, only the memory addresses in the image formation memory 36 and a read address conversion rule for reading address data corresponding to a trimming image from data stored in the memory addresses are used. Since the output signals from the secondary signal detector 19 are stored in time series in the image formation memory 36, there is no information identifying the positional information of the pixels other than the information of the data storage order. In this case, the positional relationship between adjacent pixels is established such that the pixels are substantially in parallel to the first coordinate axis 121 (which corresponds to reference numeral 114 of FIG. 4) or the second coordinate axis 122 (which corresponds to reference numeral 115 of FIG. 4).

While scanning with the electron beams, the pixels having the same scan line address are scanned according to their write order addresses, and then the next scan line is scanned. In this case, a scan area is set to include a rectangular display area 123 composed of 4 by 4 pixels, and the address of a display image in the display area 123 is determined at the same time when the scan address is determined. For clarity of description, an acquired image of 4 by 4 pixels is shown in FIG. 6. However, when all of the pixel addresses of the acquired image are included in the scan pixel addresses, the number of pixels of an acquired image may be increased. The address is represented by two character strings, but it may be represented by one character string when a scan area is two-dimensionally arranged.

Figure 7:
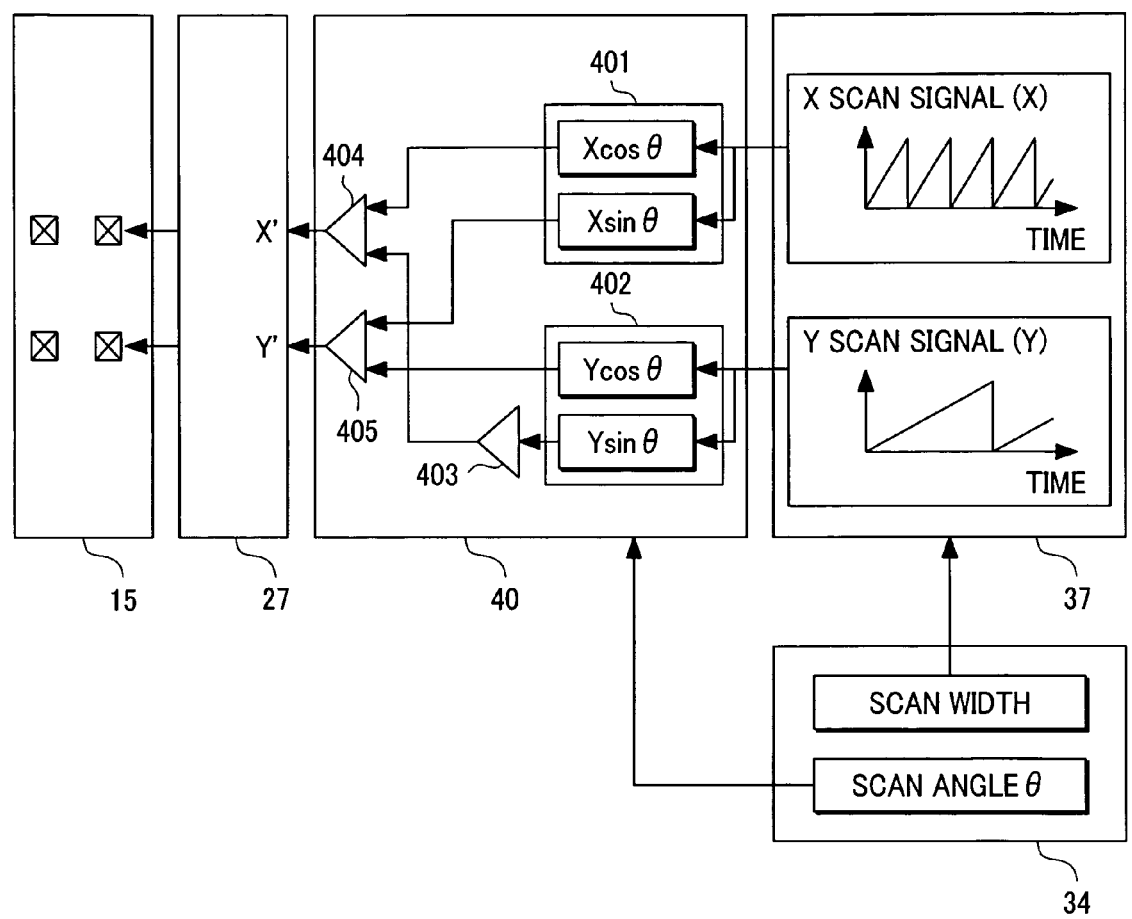
FIG. 7 is a diagram illustrating an example of a driving signal generating mechanism for radiating an electron beam in an oblique direction according to the first embodiment of the invention.

Next, the operation of the apparatus during scanning with a charged particle beam in the defect review system according to this embodiment will be described with reference to a functional block diagram. FIG. 7 shows the internal structures of the review information storage unit 34, the scan waveform forming unit 37, the angle converting unit 40, the deflection lens control power source 27, serving as a deflection controller, and the deflector coil 15, which is a scan deflector, shown in FIG. 3 and information transmitted between the units (arrows in FIG. 7). In the operation sequence of the apparatus, when the process reaches a step of capturing a defect image for search or a step of capturing a defect image for observation in the flowchart shown in FIG. 4, the review information storage unit 34 transmits information of the scan width and the scan angle θ stored in an internal memory to the scan waveform forming unit 37 and the angle converting unit 40. The scan waveform forming unit 37 generates a reference signal waveform for scanning.

The reference signal waveform is a driving signal for driving the deflector coil 15, which is a scan deflector, to move the charged particle beam radiating position in the X-axis or Y-axis direction.

In the defect review system according to this embodiment, the angle converting unit 40 performs θ conversion on the reference signal waveform generated by the scan waveform forming unit 37, thereby forming an oblique scan signal waveform. An X scan signal and a Y scan signal having intensity that varies in a sawtooth shape with time are used as the reference signal waveform. One period of the X scan signal depends on the number of pixels forming one profile line of the image in the X direction, and the amplitude of the X scan signal depends on the field of view of the image in the X direction. Similarly, one period of the Y scan signal depends on the number of pixels forming one profile line of the image in the Y direction, and the amplitude of the Y scan signal depends on the field of view of the image in the Y direction. The reason why the amplitude of the scan signal is related to the field of view of the image is that the strength of a magnetic field or an electric field that is applied to the primary charged particle beam by the scan deflector is proportional to the amplitude of the scan signal, and as the strength of the magnetic field or the electric field applied increases, the deflection width of the primary charged particle beam increases.

The generated X scan signal and Y scan signal are transmitted to the angle converting unit 40, and the angle converting unit 40 performs a rotation process on the received signals in correspondence with a set scan angle θ. The rotation process performed in the angle converting unit 40 shown in FIG. 5 is shown in the function block. The amplitude values X and Y of the X and Y scan signal waveforms generated by the scan waveform forming unit 37 are input to an X multiplier 401 and a Y multiplier 402, respectively, and the X and Y multipliers 401 and 402 multiply the received signals by sin θ and cos θ to generate data strings X sin θ, X cos θ, Y sin θ, and Y cos θ, respectively. A negative multiplier 403 multiplies the data string Y sin θ by −1 to change the data string to a negative value. The data string X cos θ among the output signals from the X multiplier 401 and an output signal from the negative multiplier 403 are input to an X adder 404, and the X adder 404 generates an X scan signal X' (.gov=X cos θ−Y sin θ) for oblique scanning. Similarly, an output signal, X sin θ, from the X multiplier 401 and an output signal, Y cos θ, from the Y multiplier 402 are input to a Y adder 405, and the Y adder 405 outputs a resultant signal X sin θ+Y cos θ as a Y scan signal Y' for oblique scanning. The above-mentioned rotation process corresponds to an operation of multiplying a vector having amplitude value data of the X scan signal and amplitude value data of the Y scan signal as its components by a rotation matrix of θ. The generated oblique scan signals are transmitted to the deflection lens control power source 27 to drive the deflector coil 15.

Figure 8:
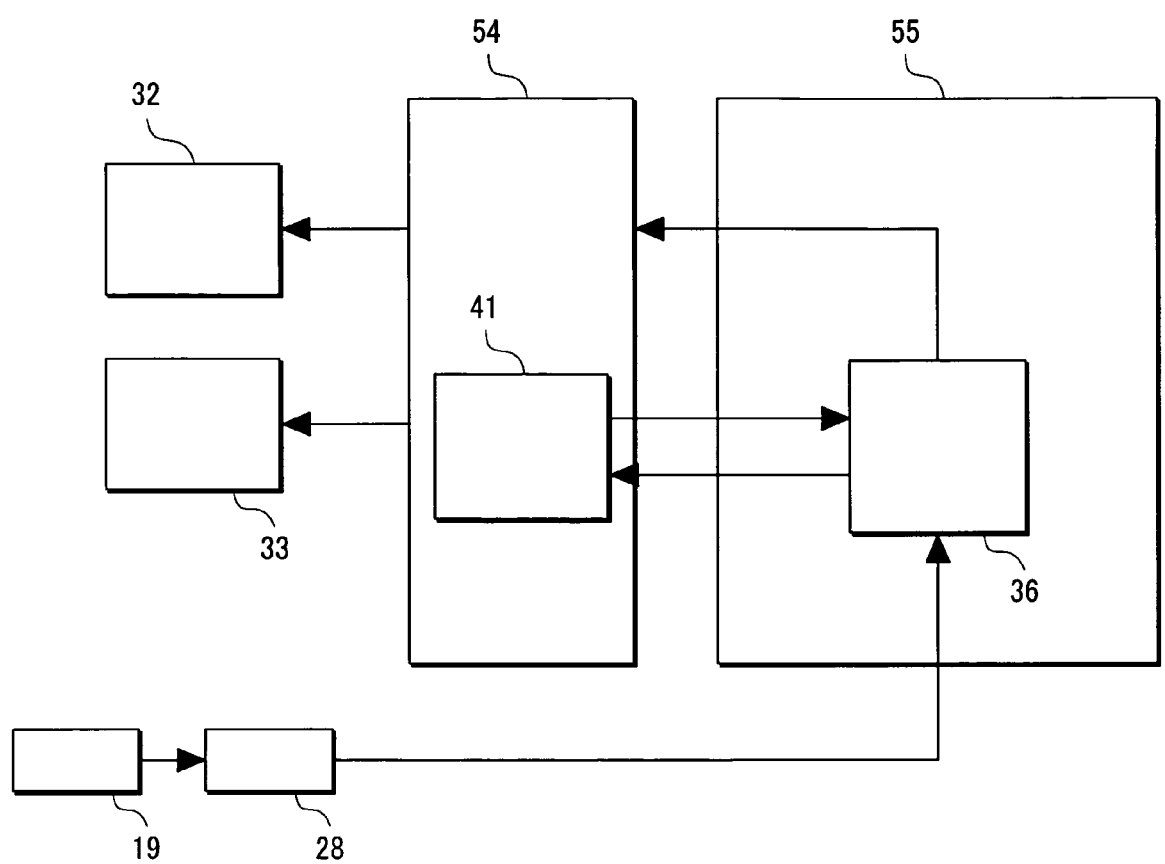
FIG. 8 is a block diagram illustrating the structure of a mechanism for writing or reading image signal data to or from an image formation memory according to the first embodiment of the invention.

Next, the operation of the apparatus performing image trimming on the oblique scan image to acquire a display image will be described with reference to FIGS. 7 and 8. The signals detected by the secondary signal detector 19 are amplified by the signal amplifiers 28 and 29. Then, the amplified signals are transmitted to the image formation memory 36 as pixel information and temporarily stored therein (see FIG. 8). In this embodiment, since the oblique scan angle θ is fixed to 45 degrees, the scan addresses for oblique scanning and the address information of the trimming area can be mathematically associated with each other, and the address information (or conversion rule information for converting the address of the trimming area into the scan address for oblique scanning) of the trimming area is stored in a memory of the image address generating unit 41 on the basis of the association.

When scanning is performed at an angle of 45 degrees with the charged particle beam, the signals detected by the secondary signal detector 19 are transmitted to the image formation memory 36 and then sequentially stored according to, for example, the addresses in the scan direction shown in FIG. 6 ((1,1), (1,2), (1,3), (1,4), (1,5), (1,6), (2,1), (2,2), (2,3), (2,4), (2,5), (2,6), (3,1), . . . ). Then, when the arithmetic unit 54 reads the address information of the trimming area or the address conversion rule information stored in the memory of the image address generating unit 41 and transmits the read information to the image formation memory 36, pixel signal data necessary to form a trimming image is read from the image formation memory 36 that temporarily stores image signal (brightness value) data, which is image information. That is, in FIG. 6, addresses ((3,3), (4,4), (5,4), (6,5), (4,3), (5,3), (6,4), (7,4), (5,2), (6,3), (7,3), (8,4), (6,2), (7,2), (8,3), and (9,3)) corresponding to the display area 123 are stored in the image formation memory 36, and the stored pixel signal data, which is a display image, is read from the image formation memory 36 and then transmitted to the image display unit 32 or the image storage unit 33. In this way, a trimming image is formed and displayed on the image display unit 32. Alternatively, the pixel signal data is temporarily stored as display image data in the image storage unit 33 and then displayed on the image display unit 32.

In this embodiment, since the display image trimmed from an oblique scan image is used, it is possible to prevent image errors in the display image, and thus acquire a clear image without brightness variation. In addition, it is possible to improve a defect recognition rate during automatic review, and prevent the erroneous recognition of display information.

Second Embodiment

Next, as a second embodiment, a process of complementing pixels when a defect review system displays an image will be described. In the second embodiment, the configuration of an apparatus, the overall process flow of a defect review system, and a method of scanning a specimen with an electron beam are the same as those in the first embodiment, and thus a description thereof will be omitted. In addition, in this embodiment, the scan angle θ may be an arbitrary value, and a process of complementing pixels of a display image is performed according to the scan angle θ, if necessary.

Figure 9:
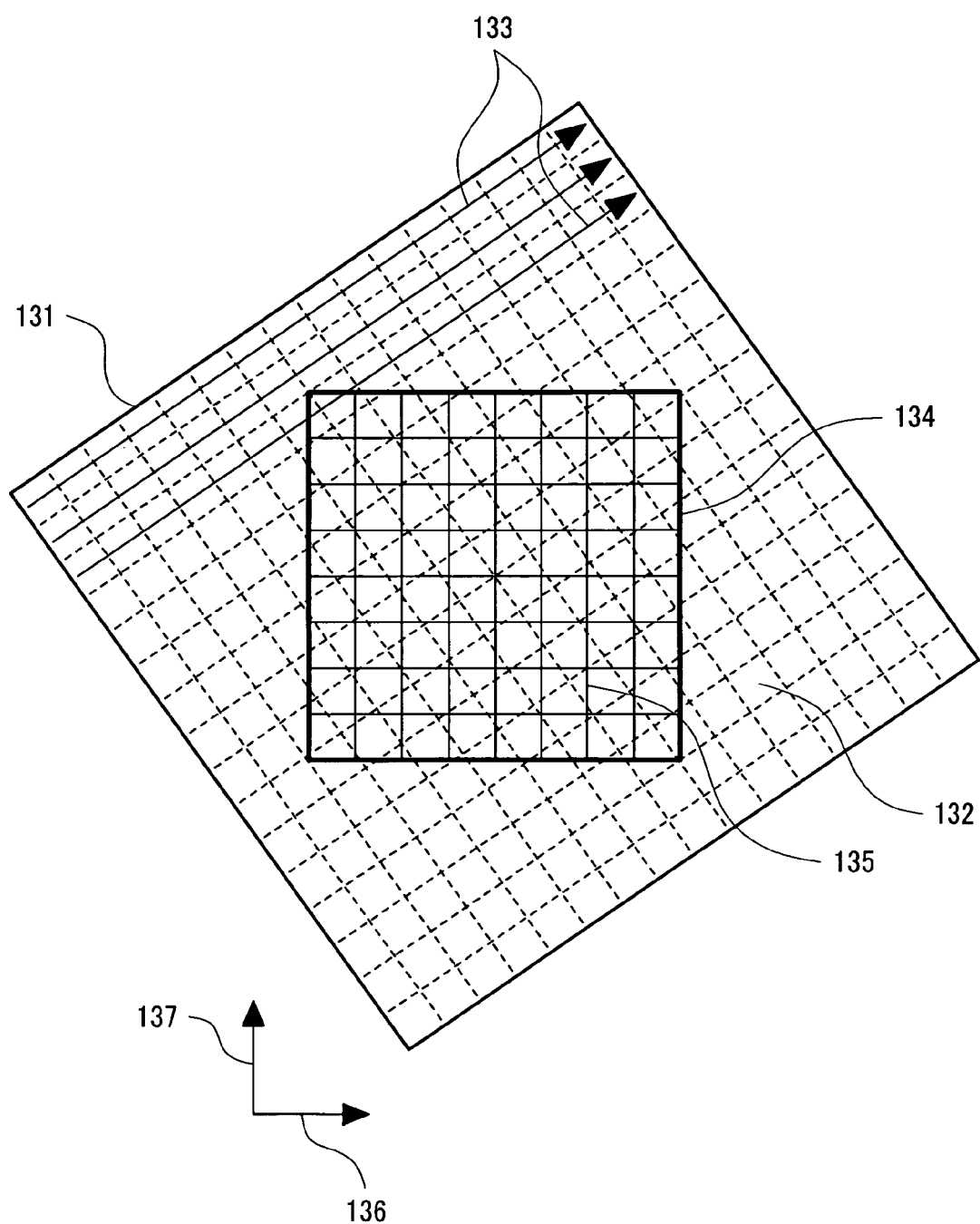
FIG. 9 is a diagram schematically illustrating the relationship between a display image and pixels in a scan area according to a second embodiment of the invention.

FIG. 9 shows acquired pixel information addresses and acquired image information addresses. In this embodiment, a rectangular coordinate is used, which is determined by wafer alignment and includes a first coordinate axis 136 (which corresponds to reference numeral 105 of FIG. 1) and a second coordinate axis 137 (which corresponds to reference numeral 106 of FIG. 1) orthogonal to the first coordinate axis 136. A scan area 131 and a display image 134 have rectangular shapes. The rectangular display image 134 is displayed such that sides thereof are substantially parallel to the first coordinate axis 114 and the second coordinate axis 115. The rectangle of the rectangular scan area 131 is equal to the rectangle of the display image 134 rotated by an angle of θ with its center of gravity as the center and then enlarged. Scanning 133 with an electron beam is performed so as to correspond to scan pixels 132 that are provided in the scan area 131 without any gap. Therefore, generally, the positions of the scan pixels 132 are not matched with the positions of display pixels 135 of the display image 134.

Figure 10:
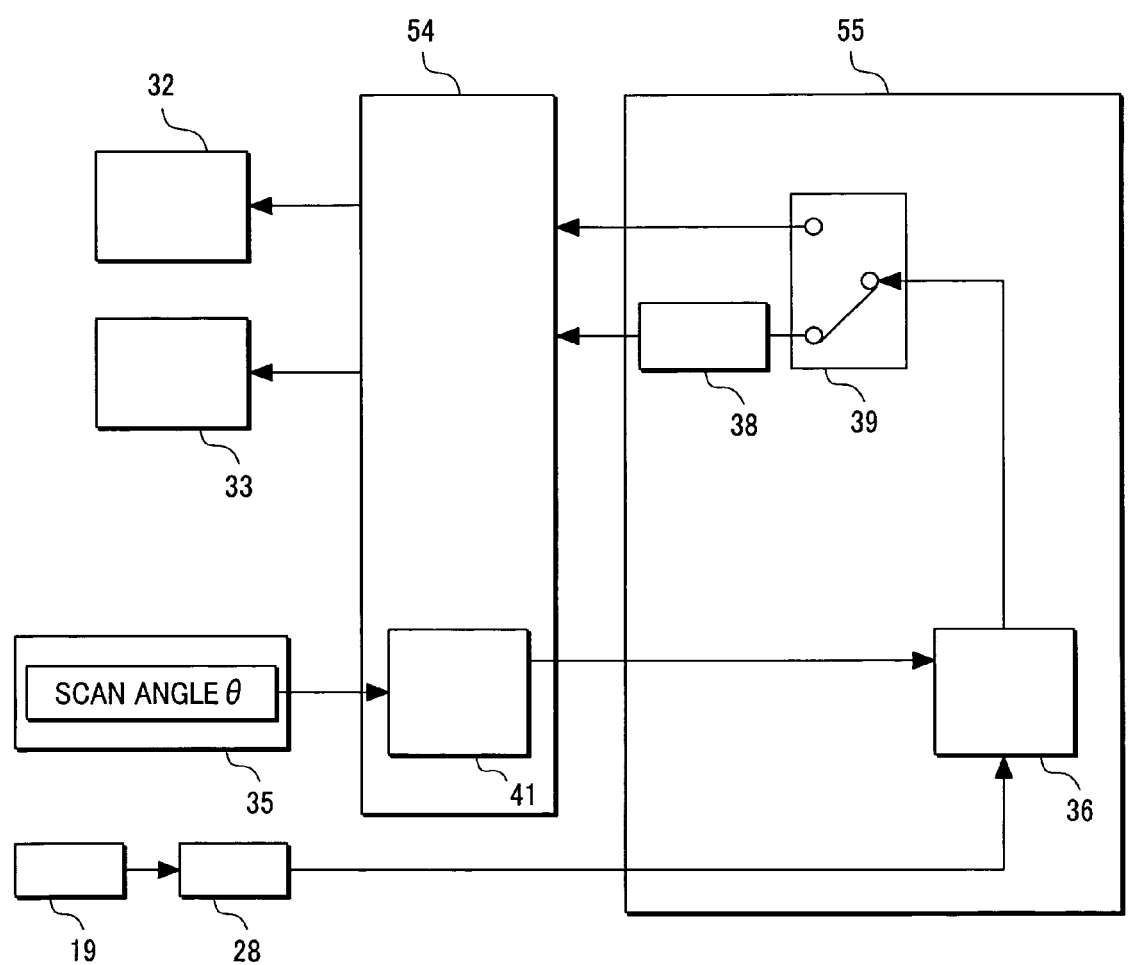
FIG. 10 is a block diagram illustrating the structure of a mechanism for writing or reading image signal data to or from an image formation memory according to the second embodiment of the invention.

FIG. 10 shows details of a method of forming an image that is obtained by a secondary signal detector 19 when this embodiment is performed. For example, signals detected by the secondary signal detector 19 are amplified by a signal amplifier 28, and then transmitted to an image formation memory 36 as pixel information. An image address generating unit 41 divides a display area, which is determined by the acquired pixel information addresses that are assigned to the pixels in the order in which the pixels are captured by scanning with an electron beam, and the scan angle θ and the scan area transmitted from an input unit 35, into the number of display pixels, and assigns the acquired image information addresses to the pixels. In this case, each of the acquired image information addresses is associated with the acquired pixel information address closest thereto and information on the positional deviation of the acquired image information address. The address information generated by the image address generating unit 41 is transmitted to the image formation memory 36. In the image formation memory 36, the addresses of pixel information are assigned in the order in which the pixel information is transmitted, and the pixels associated with the display pixel information addresses are used to form an image.

The formed image is transmitted together with the acquired pixel information addresses and the information on the positional deviation of the acquired image information addresses to the image processing unit 38 through a path selected by the signal path switching unit 39. The image processing unit 38 performs appropriate image processing, such as complementation, on the transmitted image, the acquired pixel information addresses, and the information on the positional deviation of the acquired image information addresses to generate a processed image, and transmits the processed image to the arithmetic unit 54. Then, the arithmetic unit 54 displays the image on the image display unit 32, and stores it in the image storage unit 33.

Figure 11:
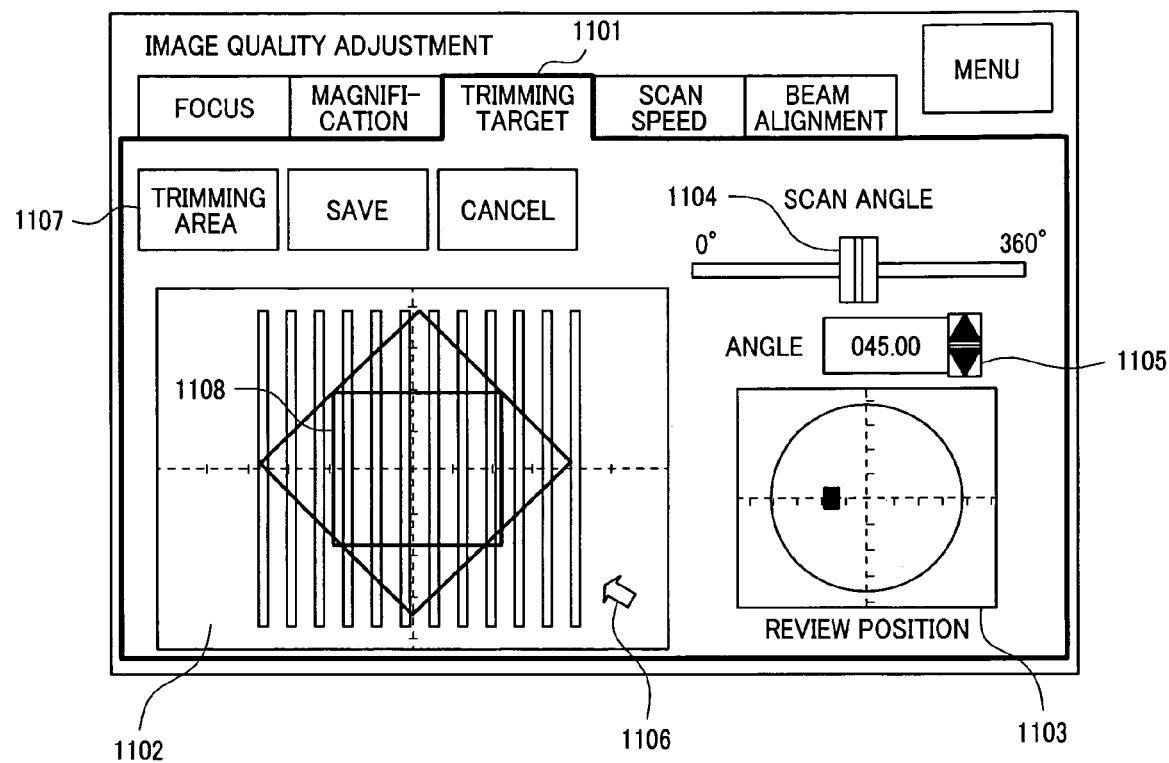
FIG. 11 is a diagram illustrating an example of the configuration of an angle setting GUI screen according to the second embodiment of the invention.

In the defect review system according to this embodiment, before a review process, the scan angle or the rotation angle of the trimming area is determined according to the type of a specimen to be reviewed. FIG. 11 shows an example of the configuration of an angle setting GUI screen. In FIG. 11, a scan angle is input on a setup screen, such as an "image quality adjustment" screen. When an operator clicks an "image quality adjustment" button on an initial setup screen, the screen shown in FIG. 11 is displayed on the image display unit 32. The operator of the apparatus selects a "trimming target" tab screen 1101 among a plurality of tabs displayed on the display screen to display a scan angle adjusting tab screen on a GUI. For example, an enlarged image 1102 of a review position, a locater 1103 that indicates where the review positions are on the entire wafer, a scroll bar 1104 for setting an angle, a save button for storing set values, and a cancel button for cancelling the set values are displayed on the tab screen 1101. Since the scan angle has not been set yet, actually, the image of an area that is scanned at a default scan angle (for example, 0°) is displayed as the enlarged image 1102 of the review position. In addition, a position that is not affected by radiation of an electron beam, such as an alignment mark, is selected as an electron beam radiation position for setting the scan angle in order to prevent a specimen from being damaged due to the radiation of an electron beam. The movement of the electron beam radiation position to the alignment mark is performed by a stage control unit (not shown) and the arithmetic unit 54, which is a host control device of the stage control unit.

The operator of the apparatus moves a cursor 1106 to move the scroll bar 1104 to an arbitrary position, thereby setting the scan angle. The user may use a button 1105 to set the angle. Since the set value of the scan angle can be changed by a minimum step size (for example, 0.01° in FIG. 11), the button 1105 can more accurately set the angle than the scroll bar 1104. The operator uses the input device 35 to operate the scroll bar 1104 and the button 1105. The set angle value is stored in the review information storage unit 34 or the memory of the arithmetic unit 54, and is read to the angle converting unit 40, if necessary.

On the GUI screen shown in FIG. 11, the user can set the size of a trimming area on the review image display screen. When the operator of the apparatus clicks a trimming area button 1107, a trimming area display pane 1108 is displayed on the screen, and the operator moves the cursor 1106 to change the size of the display pane 1108 to an arbitrary size. When the size of the trimming area and the scan angle are set, the arithmetic unit 54 calculates the size of a scan area (which corresponds to an area larger than the display pane 1108), and stores the size of the scan area in the review information storage unit 34 or the memory of the arithmetic unit 54. The scan waveform forming unit 37 refers to information on the calculated size of the scan area to use for setting the amplitude of a scan signal waveform.

The angle setting process may be performed at any point in time regardless of an operation type, such as a manual operation or an automatic operation. In particular, during the automatic operation, the angle setting according to this embodiment and the parameters required to be set in the sequence of the flowchart shown in FIG. 4, such as image magnification and a scan speed, are set as automatic review conditions. In this embodiment, the scan angle is set on the GUI screen, such as the "image quality setting screen", but it may be set on other setup screens.

In this embodiment, since the display image trimmed from the oblique scan image that is inclined at the angle selected by the user is used, it is possible to prevent image errors in the display image, and thus acquire a clear image without brightness variation. In addition, it is possible to improve a defect recognition rate during automatic review, and prevent the erroneous recognition of display information.

Although the defect review systems according to the exemplary embodiments of the invention have been described above, the invention is not limited thereto, but various modifications and changes of the invention can be made without departing from the scope and spirit of the invention. Any apparatus can be used as long as it has the same structure as the charged particle beam apparatus.

What is claimed is:

1. A charged particle beam apparatus comprising:
   a specimen chamber configured to have a specimen stage for holding a specimen to be measured provided therein; and
   a charged particle optical column configured to scan the specimen to be measured with a charged particle beam, and to detect and output secondary signals generated by scanning,
   wherein the charged particle optical column includes:
   a scan deflector configured to scan a surface of the specimen to be measured with the charged particle beam in an arbitrary direction;
   an arithmetic unit configured to acquire pixel signal data from the secondary signals generated by a radiation of the charged particle beam by the scan deflector;
   an image formation storage unit configured to store the pixel signal data; and
   an image display unit configured to display a specimen image formed by extracting a portion of the pixel signal data from the image formation storage unit,
   wherein the arithmetic unit is configured to control a scan direction of the charged particle beam to be inclined with respect to a direction in which the specimen image is extracted from the image formation storage unit, and is configured to control a size of a trimming area of the specimen image with respect to a scan area of the charged particle beam.

2. The charged particle beam apparatus according to claim 1,
   wherein when the specimen image is displayed, pixel signal data in the scan direction of the charged particle beam is extracted from the image formation storage unit and displayed on the image display unit.

3. The charged particle beam apparatus according to claim 1,
   wherein the direction in which the specimen image is extracted from the image formation storage unit is substantially parallel to coordinate axes of a rectangular coordinate system for controlling the direction in which the charged particle beam is radiated, and
   the scan direction of the charged particle beam is inclined at a predetermined angle with respect to the coordinate axes of the rectangular coordinate system.

4. The charged particle beam apparatus according to claim 3, wherein the predetermined angle is 45 degrees with respect to one of the coordinate axes of the rectangular coordinate system.

5. A charged particle beam apparatus configured to scan a specimen with a charged particle beam and forms a specimen image using secondary signals obtained by scanning, the apparatus comprising:
- a scan deflector configured to scan the specimen with the charged particle beam;
- a deflection controller configured to control a deflection operation of the scan deflector;
- a secondary signal detector configured to detect secondary signals;
- an arithmetic unit configured to output driving signals to the deflection controller in order to radiate the charged particle beam in a direction inclined with respect to a reference rectangular coordinate system of the charged particle beam apparatus; and
- an image display unit configured to display the specimen image;
- wherein the arithmetic unit includes:
- an image formation storage unit configured to store image display data on the basis of output signals from the secondary signal detector; and
- an address generating unit configured to generate read addresses for reading out the image display data of a trimming area along coordinate axes of the reference rectangular coordinate system from the image formation storage unit, thereby enabling a size of the trimming area to be controlled with respect to a scan area of the charged particle beam;
- wherein the image display unit is configured to display the image display data read from the image formation storage unit on the basis of the read addresses.

6. The charged particle beam apparatus according to claim 5,
wherein the arithmetic unit further includes:
- a scan waveform forming unit configured to generate a reference signal waveform for scanning with the charged particle beam; and
- an angle converting unit configured to perform angle conversion corresponding to the inclined direction on the reference signal waveform to output the driving signals.

7. The charged particle beam apparatus according to claim 6,
wherein the angle of the inclined direction is 45 degrees with respect to the coordinate axes of the reference rectangular coordinate system.

8. A charged particle beam apparatus comprising:
- a specimen chamber configured to have a specimen stage for holding a specimen to be measured provided therein; and
- a charged particle optical column configured to scan the specimen to be measured with a charged particle beam, and to detect and output secondary signals generated by scanning, the charged particle optical column including:
  (1) a scan deflector configured to scan a surface of the specimen to be measured with the charged particle beam in an arbitrary direction,
  (2) an arithmetic unit configured to acquire pixel signal data from the secondary signals generated by radiation of the charged particle beam by the scan deflector, configured to control a scan direction of the charged particle beam to be inclined with respect to a direction in which the specimen image is extracted from the image formation storage unit, and configured to control a size of a trimming area of the specimen image with respect to a scan area of the charged particle beam,
  (3) an image formation storage unit configured to store the pixel signal data, and
  (4) an image display unit configured to display a specimen image formed by extracting a portion of the pixel signal data from the image formation storage unit.

9. The charged particle beam apparatus according to claim 8,
wherein when the specimen image is displayed, pixel signal data in the scan direction of the charged particle beam is extracted from the image formation storage unit and displayed on the image display unit.

10. The charged particle beam apparatus according to claim 8,
wherein the direction in which the specimen image is extracted from the image formation storage unit is substantially parallel to coordinate axes of a rectangular coordinate system for controlling the direction in which the charged particle beam is radiated, and
the scan direction of the charged particle beam is inclined at a predetermined angle with respect to the coordinate axes of the rectangular coordinate system.

11. The charged particle beam apparatus according to claim 10,
wherein the predetermined angle is 45 degrees with respect to one of the coordinate axes of the rectangular coordinate system.

* * * * *